(12) United States Patent
Ballsieper et al.

(10) Patent No.: US 10,617,371 B2
(45) Date of Patent: Apr. 14, 2020

(54) GOGGLES FOR RECEIVING AT LEAST ONE RADIATION PROTECTION MATERIAL

(71) Applicant: MAVIG GMBH, Munich (DE)

(72) Inventors: Barbara Ballsieper, Munich (DE); Martin Schmid, Munich (DE)

(73) Assignee: MAVIG GMBH, Munich (DE)

( * ) Notice: Subject to any disclaimer, the term of this patent is extended or adjusted under 35 U.S.C. 154(b) by 165 days.

(21) Appl. No.: 15/868,108

(22) Filed: Jan. 11, 2018

(65) Prior Publication Data

US 2018/0192971 A1 Jul. 12, 2018

(30) Foreign Application Priority Data

Jan. 12, 2017 (DE) .................... 10 2017 200 437

(51) Int. Cl.
   *G02C 7/10* (2006.01)
   *A61B 6/10* (2006.01)
   *A61F 9/02* (2006.01)
   *A61N 5/10* (2006.01)
   *G21F 3/02* (2006.01)

(52) U.S. Cl.
   CPC .............. *A61B 6/107* (2013.01); *A61F 9/022* (2013.01); *A61F 9/026* (2013.01); *A61F 9/027* (2013.01); *A61F 9/029* (2013.01); *A61N 5/10* (2013.01); *G21F 3/02* (2013.01); *A61N 2005/1089* (2013.01); *A61N 2005/1094* (2013.01)

(58) Field of Classification Search
   CPC .... G02C 2202/16; G02C 7/104; G02C 7/107; G02C 7/10; A61F 9/023; A61F 9/022
   USPC .................................. 351/43, 44; 2/428, 432
   See application file for complete search history.

(56) References Cited

U.S. PATENT DOCUMENTS 2,204,631 A 12/1937 Tillyer
4,021,862 A 5/1977 Glasser et al.
(Continued)

FOREIGN PATENT DOCUMENTS

DE 1544769 11/1971
DE 2221922 11/1973
(Continued)

OTHER PUBLICATIONS

EESR dated Jun. 7, 2018 issued is corresponding EP Patent Appln. No. 18151063.7.

*Primary Examiner* — Hung X Dang
(74) *Attorney, Agent, or Firm* — Scully Scott Murphy and Presser

(57) ABSTRACT

The present invention relates to goggles, in particular radiation protection goggles, for receiving at least one radiation protection material which protects the eyes of a patient from radiation being harmful to the eyes, in particular β-radiation and/or x-ray radiation and/or gamma radiation. The goggles comprise: two goggle frames, each having a continuously circumferential side wall structure completely enclosing an area around the respective eye of the patient, a length-adjustable connection element between the two goggle frames in the area of the patient's nose in order to change the distance between the two goggle frames relative to one another, and at least one length-adjustable holding element for fixing the two goggle frames at the patient's head. The side wall structures are configured for receiving at least one radiation protection material substantially completely around its circumference.

14 Claims, 3 Drawing Sheets

(56) References Cited

U.S. PATENT DOCUMENTS

| | | | |
|---|---|---|---|
| 4,024,405 A | | 5/1977 | Szot |
| 5,016,292 A | | 5/1991 | Rademacher |
| 5,422,684 A | | 6/1995 | Keller |
| 6,119,278 A | * | 9/2000 | Kawashima ......... A63B 33/002 2/428 |
| 7,897,989 B2 | | 3/2011 | Kumura |
| 2008/0273165 A1 | | 11/2008 | Mankovitz et al. |
| 2014/0041105 A1 | | 2/2014 | Zemlak |
| 2017/0351121 A1 | | 12/2017 | Wang |

FOREIGN PATENT DOCUMENTS

| | | |
|---|---|---|
| DE | 3116760 A1 | 11/1982 |
| DE | 227267 A1 | 9/1985 |
| DE | 9314811.9 U1 | 1/1994 |
| DE | 9414879.1 U1 | 1/1995 |
| EP | 1623690 A2 | 2/2006 |

* cited by examiner

GOGGLES FOR RECEIVING AT LEAST ONE RADIATION PROTECTION MATERIAL

The invention relates to goggles for receiving at least one radiation protection material which protects the eyes of a patient from radiation being harmful to the eyes, in particular β-radiation and/or x-ray radiation and/or gamma radiation. The present invention in particular relates to the use of the goggles according to the invention as radiation protection goggles or radiation eye shield for protecting the eyes of a patient from radiation being harmful to the eyes, in particular β-radiation and/or x-ray radiation and/or gamma radiation.

Various radiation protection goggles are known in the art.

DE 31 16 760 A1 relates to radiation protection goggles having a flexible supporting body whose edge fits well against the head of the person wearing the goggles and which comprises a laser radiation shield that prevents radiation incident from the side from entering the eyes of the person wearing the goggles. The radiation protection goggles further comprise at least one metal layer extending up to the region of the edge of the supporting body that is intended for fitting against the head of the person wearing the goggles. The metal layer can be a metal sheet of aluminum embedded in the supporting body.

U.S. Pat. No. 4,024,405 A relates to an x-ray eye shield, wherein the eye shield conforms to the contour of the head around the eyes and consequently also protects from x-rays incident from the side. For this purpose, a lead film is incorporated into a plastic material.

DE 94 14 879 U1 and DE 93 14 811 U1 relate to radiation protection goggles, in particular for providing protection from laser radiation, which comprise at least one protective filter and a goggle frame. The inner insert is made of a skin-friendly elastomer which can absorb laser radiation hitting it.

U.S. Pat. No. 5,016,292 A relates to goggles protecting from, e.g., UV, gamma and x-ray radiation. The goggles are designed to protect the eyes from radiation from all possible directions. The lens 8 of the goggles is made of a polymer that is charged with lead.

U.S. Pat. No. 4,021,862 A relates to a radiation eye shield protecting from ionizing radiation from various directions, wherein the viewing windows and the remaining shield of the goggles are made of materials that are charged with lead.

DD 227 267 A1 relates to protective goggles having a length-adjustable bridge and provide for a particular sealing in the nasal region, in particular for protection from radiation. The goggle frame halves comprise nose-bridge structures which taper off in a quarter arch and end in a flat stop.

In summary, a plurality of radiation protection goggles are known in the art. However, all known radiation protection goggles are designed to provide protection from a specific radiation. The laser-radiation protection goggles are not suitable for being used as protection from x-ray radiation because of the much higher wavelength of laser radiation as compared to x-ray radiation.

In other words, none of the above-mentioned radiation protection goggles is configured for being used for various purposes.

Furthermore, CT radiation protection devices for the eyes are available in the market, for example marketed by the companies SOMATEX Medical Technologies ("CT-Eye-ProteX"), F & L Medical Products ("AttenuRad CT Eye Shield") and Kemmetech Ltd. ("GreyShield Eye Protection Shield"). These radiation protection devices cover the eyes completely so that the patient has no chance to read something while being examined. Moreover, these radiation protection devices only rest on the eyes and thus no stable positioning can be guaranteed when the patient moves while being examined.

Moreover, none of the radiation protection devices available from the above-mentioned companies is configured for being used for various purposes.

It is an object of the present invention to provide radiation protection goggles which avoid or reduce the disadvantages of the prior art. In particular, it is an object of the present invention to provide radiation protection goggles which can be used for various kinds of radiation and are suitable for being used for computer tomography and radio therapy.

These objects are achieved by the features of the independent claims. The dependent claims relate to further aspects of the invention.

According to an aspect of the present invention, goggles are provided, in particular radiation protection goggles, for receiving at least one radiation protection material which protects the eyes of a patient from radiation being harmful to the eyes, in particular β-radiation and/or x-ray radiation and/or gamma radiation. The goggles comprise: two goggle frames, each having a continuously circumferential side wall structure completely enclosing an area around the respective eye of the patient, a length-adjustable connection element between the two goggle frames in the area of the patient's nose in order to change the distance between the two goggle frames relative to one another, and at least one length-adjustable holding element for fixing the two goggle frames at the patient's head, wherein the side wall structures are configured for receiving at least one radiation protection material substantially completely around its circumference.

The present invention starts out from the basic idea that any radiation protection material can be incorporated into the radiation protection goggles. In particular, this means that the basic shape of the radiation protection goggles is likewise suitable for being used as β-radiation protection goggles, as x-ray radiation protection goggles or as gamma radiation protection goggles. Thus, it is possible to use the radiation protection goggles also for various kinds of rays, if desired.

The radiation protection material is received by the side wall structure substantially completely around its circumference. In other words, the side wall structure is configured for receiving at least one radiation protection material as completely as possible around its circumference. Thus, the eye is shielded effectively from radiation incident from the side. An area around the eye that is as large as possible thus can be shielded sufficiently from radiation being harmful to the eye, in particular from radiation incident from the side.

The side wall structure can have an inner side wall and an outer side wall which are preferably connected by a base wall at an end of the side wall structure.

The inner side wall and the outer side wall are preferably spaced by a predetermined distance in the cross direction to the viewing direction of the patient so that a space is formed, wherein the space is configured for receiving the at least one radiation protection material which is preferably configured for filling the gap completely in the longitudinal direction.

The predetermined distance, i.e. the space, can be, for example, 0.5 mm, preferably 1 mm and particularly preferably 2 mm.

Moreover, the space can vary in the circumferential direction of the goggle frames.

The space can have a conical shape from the upper side of the goggles (distal end) towards the lower side of the goggles (proximal end). This is advantageous in view of injection molding and in view of stability.

As described above it is preferred that the radiation protection material fills the space completely in the longitudinal direction. The longitudinal direction extends perpendicular with respect to the distance vector between the inner side wall and the outer side wall. The fact that the space is filled completely in the longitudinal direction allows a protection from radiation incident from the side that is as effective as possible.

The radiation protection material can fill the space in the cross direction to the longitudinal direction partly or completely. The distance between the inner side wall and the outer side wall is preferably not filled completely with radiation protection material.

Alternatively, the at least one radiation protection material is applied to the above-mentioned side wall structure without a space being formed by means of an inner side wall and an outer side wall. For example, the radiation protection material can be bonded to the side wall structure.

The specific purpose of the radiation protection goggles is preferably determined by loading the space (gap between the inner side wall and the outer side wall) with the radiation protection material.

The at least one radiation protection material can comprise a first material layer formed of a material having a low atomic number Z, in particular Al, and/or a second material layer formed of a material having a high atomic number Z, in particular lead or lead replacement materials such as bismuth, tungsten, tantalum or compounds of these metals. The first material layer and the second material layer are preferably provided as a compound layer, as a thin film or as a powder dispersed in a matrix material or as a liquid for casting or injection molding.

In particular the embodiment having a space allows the material layer to be introduced as a liquid (also referred to as filler or filling material) during a casting or injection molding process. In this case, the space is filled completely with the filling material, substantially without any air inclusions.

The use of the above-mentioned casting or injection molding process is characterized i.a. by its simple principle. Since the outer side wall forms a cavity (space) together with the inner side wall, it is possible to introduce, for example, a liquid polymer which is loaded with radiation protection additives into the cavity. This process is very simple in terms of production and in principle can be used analogously to typical processes which are used in the electronics industry for encapsulating electronic circuits in which epoxy resins are used for filling the cavity.

Within the present disclosure, the boundaries between a low-Z material and a high-Z material are preferably between atomic numbers 70 and 50 and particularly preferably at 60. Even if the two ranges overlap in view of the atomic number 60, the high-Z material is always different from the low-Z material in order to meet the different absorption requirements.

Examples of low-Z materials are aluminum, tin, antimony, iodine, cesium, barium, lanthanum, cerium, praseodymium, neodymium. One or more of these elements can additionally be mixed with elements which do not belong to this group, for example rare earth elements having an atomic number Z of 60 to 70, preferably samarium, gadolinium, terbium, and/or erbium and/or ytterbium, are suitable for being additionally used in such a mixture.

Particularly preferable as a low-Z material is also chlorine having the atomic number Z=17. Chlorine is typically used in polymer chemistry as an element having a high atomic number. Thus, chlorine is also particularly preferred for the present invention.

In materials having an atomic number of smaller than/equal to chlorine (Z=17), the emission of braking radiation increases when said materials are used as beta radiation protection goggles. Thus, the radiation-protecting effect of the low-Z material for shielding beta radiation can decrease in sum. For this reason, materials having an atomic number of smaller than/equal to chlorine are preferably used.

For example bismuth, tungsten and tantalum are suitable as high-Z materials. Also lead or lead replacement materials are suitable as high-Z materials.

The first material layer can be arranged in the space neighboring the outer side wall and the second material layer can be arranged in the space neighboring the inner side wall.

Such a layer structure is particularly advantageous when the goggles are used as beta radiation protection goggles, when the first material layer is formed of a low-Z material and the second material layer is formed of a high-Z material. Thus, the outer low-Z material layer can absorb beta rays hitting it, and the inner high-Z material layer can absorb accordingly generated secondary braking radiation.

The term "absorb" does not only mean a complete absorption of the incident radiation but also a partial absorption of the radiation, i.e. a weakening of the incident radiation.

For the use as beta radiation protection goggles and/or as CT radiation protection goggles (x-ray radiation protection goggles), for example a lead film (high-Z material) having a predetermined lead equivalent value, in particular of 0.127 mm Pb, and an aluminum film (low-Z material) having a thickness of 0.1 mm are suitable.

The possible dimensions such as thickness of the layer or layers for the radiation protection materials are determined in accordance with the width of the space. In a space of 2 mm, for example radiation protection materials having a thickness of about 1.6 mm (insertion tolerances being subtracted) can be introduced. Within this thickness of 1.6 mm it is possible to arbitrarily vary the thicknesses of, e.g., two radiation protection materials, low-Z and high-Z materials, e.g. films. In this example films having a thickness ranging from 0.05 mm to 1.55 mm are preferably used, wherein the sum of the thicknesses of both films is preferably about 1.6 mm.

If the space is filled in the casting or injection molding process described above, the space is preferably filled completely, wherein no tolerance is necessary for the filling.

The goggles can further comprise an element which is transmissive to visible light and arranged preferably in the area of the distal end of each goggle frame.

The inner side wall can have a smaller height in the distal direction than the outer side wall, wherein the transmissive element is substantially flush with the outer side wall and/or rests against the distal end of the inner side wall.

Preferably, the transmissive element is connected to the side walls in a chemically tight manner A chemically tight connection between the transmissive element and the side walls can be achieved by dissolving the plastic materials with solvents at the respective boundary surfaces. Such a method is also known as "cold welding of plastic materials". This is advantageous in that it is possible to use heavy metals as radiation protection material.

The light transmissive element allows the patient to view through the radiation protection goggles during examination or therapy and to implement activities such as, e.g., reading. For example, this is particularly preferred in relatively long examinations or therapies, e.g., beta radiation therapy.

The light transmissive element can comprise a radiation protection material, in particular low-Z materials, in particular acrylic glass, or plastic materials loaded with high-Z materials, in particular bismuth or lead acrylic.

For example, the light transmissive element can comprise a plastic material having a predetermined thickness, in particular 3 mm. This thickness is particularly advantageous for providing protection from beta radiators because this thickness effectively absorbs beta radiation while producing little braking radiation.

The protection from beta radiation of a plastic material is substantially determined by the maximum energy of the beta radiation. If beta radiation is emitted, for example, by rhenium-188 (maximum energy beta radiation=2.1 MeV), the thickness of the plastic material of the light transmissive element is preferably 3 mm.

In general, a plastic material having a thickness of 1 mm provides protection from about 1 MeV of kinetic energy of the beta particles. For example, the thickness of the light transmissive material can be adapted on the basis of the specific beta radiator. The typical energy range for beta radiators lies in the range of about 20 keV ($^3$H) to about 5.4 MeV ($^{20}$F). The thickness of the light transmissive element preferably ranges between about 20 µm and about 5.5 mm.

Alternatively, when being used in goggles protecting from x-ray radiation and/or gamma radiation, the light transmissive element can also comprise lead acrylic having a predetermined thickness, in particular 3 mm, with a predetermined lead equivalent value, in particular of 0.127 mm Pb. This configuration is particularly advantageous for protection from primary and/or secondary braking radiation (also called scattered radiation) up to about 50 keV.

This allows an effective protection from radiation hitting the eyes from the front. It is thus possible to provide for an effective protection from radiation from all directions.

The goggles can further comprise a first eye provided at the part of the respective side wall structure of a goggle frame facing the nose for attaching the connection element and/or further comprise a second eye provided at the part of the respective side wall structure of a goggle frame opposite the part facing the nose for attaching the holding element.

In particular, the holding element is suitable for fixing the goggles to the patient's head. The holding element is preferably made of an elastic material, e.g. an elastomer, which extends from a second eye of the right goggle frame around the patient's head continuously up to the second eye of the left goggle frame.

Alternatively, the holding element can comprise a substantially stiff (rigid) material which is suitable for being attached to the ears of the patient.

The holding element can also be attached without a second eye directly to the side wall structure.

It is preferred to provide first and second eyes for being able to replace the connection element and/or the holding element easily.

The shape and size of the light transmissive element are preferably substantially adapted to the shape and size of the inner circumference of the outer side wall.

The side wall structure, in particular the proximal end of the side wall structure, can have a shape and/or size being ergonomically adapted to the shape of the patient's head in the area around the eyes.

The present invention further relates to the use of the goggles as described above as radiation protection goggles for protecting the eyes of a patient from radiation being harmful to the eyes, in particular β-radiation and/or x-ray radiation and/or gamma radiation.

The present invention is particularly advantageous for being used as radiation protection means for beta emitters as used, e.g., in connection with rhenium tumor therapy. In the rhenium tumor therapy, the beta radiator is placed in an open manner onto the place to be treated, for example in the face of a patient, in order to treat the tumor. A paste loaded with a beta radiator is preferably applied for this purpose. The radiation emitted by the beta radiator should not hit the eyes of the patient. For protecting the eyes of the patient from the emitted beta radiation, radiation protection goggles as described above can be used.

Since these therapies can typically last for 30 to 60 minutes or longer, the radiation protection means should be placed as firmly as possible. Moreover, the patient should be given the chance to read or the like while being treated.

Radionuclides typically do not emit only beta radiation but additionally also gamma radiation. This is due to the fact that after having emitted the beta radiation, the atoms are still in an excited state and fall back into the energetically preferred ground state after having emitted the gamma radiation. This physical property in turn has fundamental consequences on the technical realization of a radiation protection means for such beta emitters.

Typical energies for the occurring gamma rays are higher than in diagnostic beta radiation (>120 keV). Therefore, radiation protection goggles which are used as beta radiation eye shield should protect from both beta radiation and low-energy braking or gamma radiation (<120 keV). This is possible in a particularly advantageous manner by using a low-Z material and a high-Z material as described above.

Moreover, goggles designed in this manner, i.e. comprising low-Z material and high-Z material, can also be used as CT radiation protection goggles for patients because the high-Z material is also suitable for providing protection from direct x-ray radiation.

A combination of a low-Z material and a high-Z material is therefore advantageous for being used in rhenium tumor therapy for several reasons. A plastic material, respectively aluminum (or a comparable low-Z material), is an effective shield from beta radiation and minimizes the generation of braking radiation. At the same time the layer being closer to the eye (high-Z material) effectively absorbs the generated braking radiation and the gamma radiation component of the radioisotope.

In accordance with the selected technical realization of the radiation protection goggles, it is additionally possible to adjust the layer thickness for high-Z and low-Z materials in accordance with the energy of the types of radiation depending on the radioisotopes used for the therapy.

With a high-energy beta component it can be advantageous to use a relatively thick layer of low-Z material. While with a high-energy gamma component a relatively thick layer of high-Z material can be used. In the present case solely the available width of the space between the inner and the outer side wall is an edge condition for the layer thicknesses.

The features described on the basis of the beta radiator analogously also apply to x-ray radiators.

Furthermore, the goggles according to the invention are advantageous because, due to their specific design comprising two frames and a connection element provided therebetween, the goggles take a space that is as small as possible. Therefore, it is possible to apply the paste containing the beta radiator extensively on skin areas attacked by a tumor.

In the following, the present invention will be explained in more detail on the basis of embodiments and the Figures.

PREFERRED EMBODIMENTS

With reference to FIGS. 1a to 1e, an exemplary embodiment of a goggle frame for radiation protection goggles will be described in the following.

The goggle frame shown in FIGS. 1a to 1e corresponds to a goggle frame for the left eye of a patient. However, the description accordingly also applies to a goggle frame for the right eye, wherein in this case the elements are mirrored as compared to the presently shown goggle frame for the left eye, so that the connection elements of the goggle frames for the right and the left eye, which are described below, face each other for being connected with a connection element.

Figure 1A:
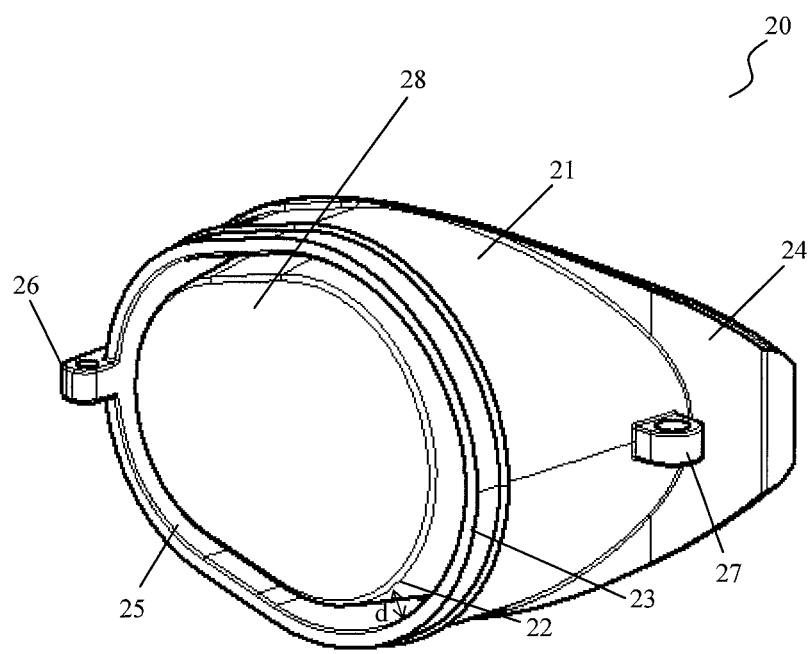
FIG. 1a shows a perspective view according to an embodiment of a goggle frame for goggles according to the invention.

FIG. 1a shows a perspective view of the goggle frame 20 according to an exemplary embodiment. The goggle frame 20 comprises a side wall structure 21 having an inner side wall 22 and an outer side wall 23.

The side wall structure 21, i.e. the inner and the outer side wall 22, 23, has a substantially oval shape to cover an area around the eye of the patient at the side as completely as possible.

The inner and the outer side wall form a space 25 having a distance d. The distance d of the space can lie, for example, in a range of 0.5 mm to 2 mm and preferably be 1 mm. The distance preferably varies across the circumference of the goggle frame 20. As described below on the basis of FIG. 1e, the distance at the side opposite the nose is preferably wider than the distance at the side facing the nose.

The goggle frame 20 further comprises a base wall 24. The base wall has a shape that conforms to the shape of the area around the eye in order to rest against the face, i.e. the skin of the patient as tightly as possible.

Moreover, the goggle frame 20 comprises a first eye 26 which is provided at the part of the side wall structure 21 of the goggle frame 20 facing the nose. The eye 26 serves for attaching a connection element 30 (see FIG. 2).

The goggle frame additionally comprises a second eye 27 which is provided at the part of the side wall structure 21 of the goggle frame 20 opposite the part facing the nose. The eye 27 serves for attaching a holding element 40 (see FIG. 2).

The side wall structure 21 defines a first opening 28 at the distal end of the goggle frame 20 through which the patient can look. The opening 28 can comprise a light transmissive element 50 (see FIG. 2).

Figure 1B:
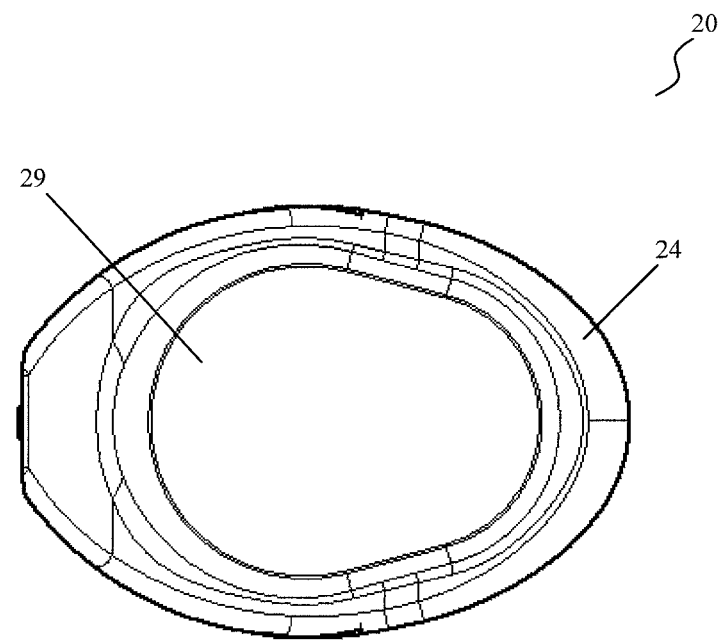
FIG. 1b shows a rear view according to the embodiment of a goggle frame for goggles according to the invention.

FIG. 1b shows a rear view of the goggle frame 20 according to FIG. 1a. In FIG. 1b the base wall 24 is particularly clearly visible. The base wall 24 is located at the rear of the goggle frame 20, i.e. the side resting against the face of the patient when he/she puts on the goggles.

The base wall 24 connects the inner and the outer side wall 22, 23 at their proximal ends. The base wall 24 defines a second opening 29 at the proximal end of the goggle frame 20 through which the patient can look.

The first opening 28 and the second opening 29 are aligned with each other in the direction extending from the distal end to the proximal end, so that the patient can look through both openings 28, 29.

Figure 1C:
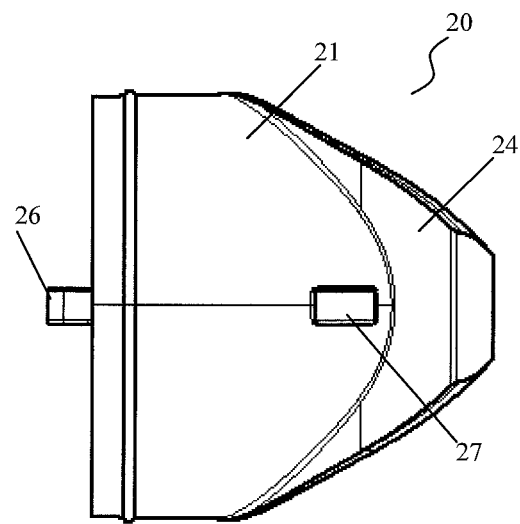
FIG. 1c shows a first side view according to the embodiment of a goggle frame for goggles according to the invention.

FIG. 1c shows a side view of the exemplary embodiment according to FIG. 1a. FIG. 1c shows the side of the goggle frame 20 facing away from the nose of a patient.

In particular, FIG. 1c shows the side wall structure 21, the base wall 24, the first and the second eye 26, 27.

The first eye 26 extends beyond the front, i.e. at the distal end, of the side wall structure 21. This allows a particularly advantageous attachment of a connection element 30 (see FIG. 2) at a certain distance from the nose of the patient.

Moreover, FIG. 1c shows the attachment of the second eye 27 to the side wall structure 21. The second eye 27 is preferably arranged in the proximal area of the side wall structure 21 to allow the goggle frames 20 to be fixed to the head of the patient in an advantageous manner.

Figure 1D:
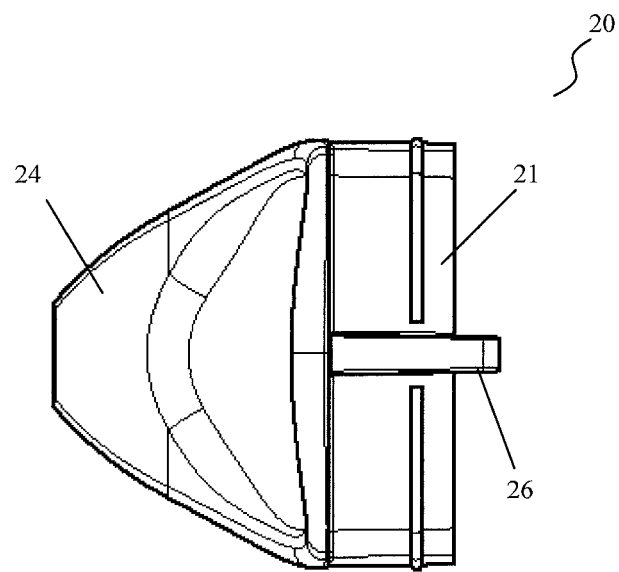
FIG. 1d shows a second side view according to the embodiment of a goggle frame for goggles according to the invention.

FIG. 1d shows a side view of the exemplary embodiment according to FIG. 1a. FIG. 1d shows the side of the goggle frame 20 facing the nose of a patient.

In particular, FIG. 1d shows the side wall structure 21, the base wall 24 and the first eye 26. As shown in FIG. 1d, the eye 26 is attached to the side wall structure 21 and, at the distal end of the side wall structure 21, projects beyond the side wall structure 21 to the front.

Figure 1E:
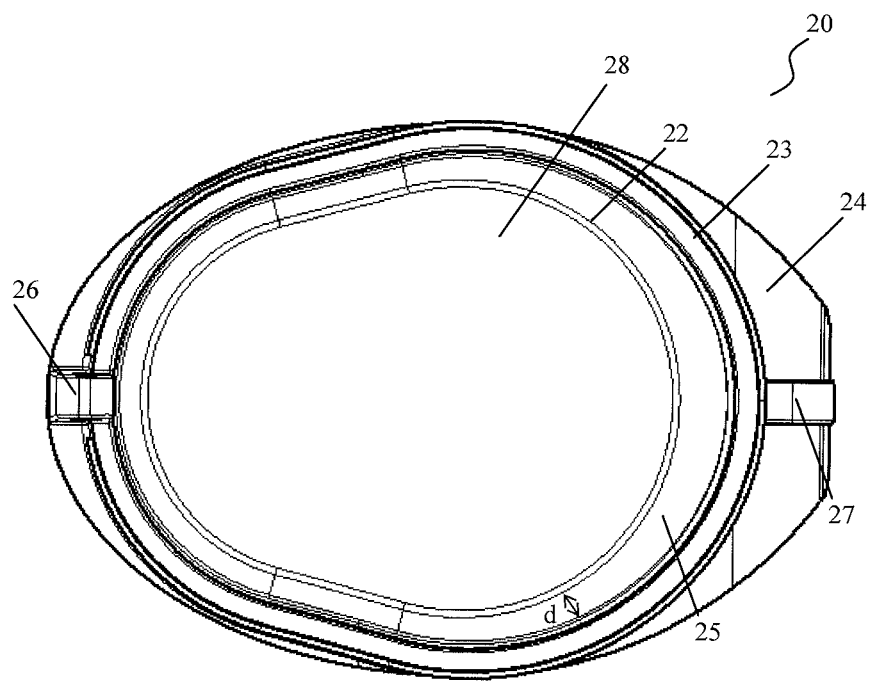
FIG. 1e shows a front view according to the embodiment of a goggle frame for goggles according to the invention.

FIG. 1e shows a front view of the exemplary embodiment according to FIG. 1a. In particular, FIG. 1e shows the inner and the outer side wall 22, 23, the base wall 24, the space 25, and the first and the second eye 26, 27.

In FIG. 1e the distance d of the space at the side of the goggle frame 20 facing away from the patient's nose is wider than the space at the side of the goggle frame 20 facing the patient's nose. The space widens gradually towards the side of the goggle frame 20 facing away from the patient's nose.

Figure 2:
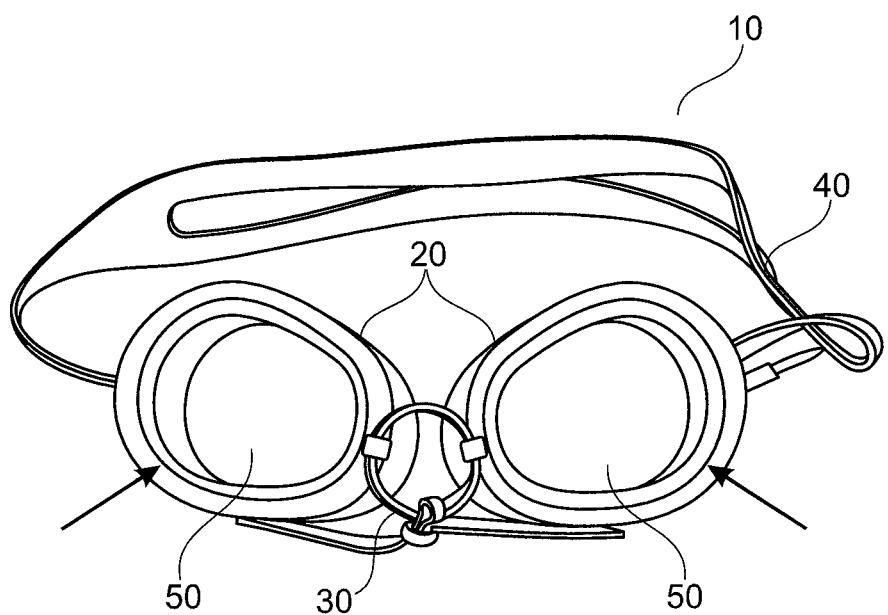
FIG. 2 shows a schematic drawing according to an embodiment of goggles according to the invention.

FIG. 2 shows an exemplary embodiment of the goggles, i.e. the radiation protection goggles. In particular, FIG. 2 shows two goggle frames 20 which are configured as exemplarily described above. Therefore, reference is made to the description of FIGS. 1a to 1e.

In addition to the goggle frames 20, the goggles 10 according to FIG. 2 show a connection element 30, a holding element 40 and a light transmissive element 50.

Moreover, the arrows identify the radiation protection material, preferably comprising a low-Z material and a high-Z material, introduced into the space 25 described above (see FIGS. 1a to 1e).

The connection element 30 and the holding element 40 are adjustable so that the goggles 10 can be used for different patients having different head sizes and head shapes, in particular different distances between the eyes.

The light transmissive element 50 closes the opening 28 at the distal end of the side wall structure 21 and allows the patient to look through the light transmissive element while being treated.

While the present invention has been described and shown with reference to its preferred embodiments, it is obvious to persons skilled in the art that various modifications and changes can be made without leaving the scope of protection of the invention. It is thus intended that the present invention covers the modifications and changes of this invention provided that they are covered by the scope of protection of the enclosed claims and their equivalents. In particular, it is clear to the person skilled in the art that the features that have been described in connection with a specific preferred embodiment can also be combined with features of other embodiments.

The invention claimed is:

1. Goggles for receiving at least one radiation protection material which protects the eyes of a patient from radiation being harmful to the eyes, wherein the goggles comprise:
   two goggle frames each comprising a continuously circumferential side wall structure completely enclosing an area around the respective eye of the patient,
   a length-adjustable connection element between the two goggle frames in the area of the nose of the patient for changing the distance between the two goggle frames relative to one another, and
   at least one length-adjustable holding element for fixing the two goggle frames to the head of the patient,
   wherein the side wall structures are configured for receiving at least one radiation protection material substantially completely around its circumference,
   wherein each side wall structure comprises an inner and an outer side wall which are connected by means of a base wall at an end of the side wall structure, wherein the inner and the outer side wall have a predetermined distance in the cross direction to the viewing direction of the patient in order to form a space, the space being configured for receiving the at least one radiation protection material.

2. The goggles according to claim 1, wherein the at least one radiation protection material is configured so as to fill the space completely in the longitudinal direction.

3. The goggles according to claim 2, comprising a light transmissive element which is preferably arranged in the area of the distal end of each goggle frame, wherein preferably the inner side wall has a smaller height in the distal direction than the outer side wall, wherein the transmissive element is substantially flush with the outer side wall and/or rests against the distal end of the inner side wall.

4. The goggles according to claim 3, wherein the light transmissive element comprises a radiation protection material.

5. The goggles according to claim 4, wherein said radiation protection material is a low-Z material.

6. The goggles according to claim 5, wherein said low-Z material is acrylic glass or plastic materials loaded with high-Z materials.

7. The goggles according to claim 6, wherein said high-Z materials are bismuth or lead acrylic.

8. The goggles according to claim 3, wherein the shape and size of the light transmissive element are substantially adapted to the shape and size of the inner circumference of the outer side wall.

9. The goggles according to claim 1, wherein the at least one radiation protection material comprises a first material layer formed of a material having a low atomic number Z, and/or a second material layer formed of a material having a high atomic number Z, wherein the first material layer and the second material layer are provided as a compound layer, as a thin film or as a powder dispersed in a matrix material or as a liquid for casting or injection molding.

10. The goggles according to claim 9, wherein the first material layer is arranged in the space neighboring the outer side wall and the second material layer is arranged in the space neighboring the inner side wall.

11. The goggles according to claim 9, wherein said first material layer is Aluminum and said second material layer is lead or lead replacement materials such as bismuth, tungsten, tantalum or compounds of these metals.

12. The goggles according to claim 1, further comprising a first eye provided at the part of the respective side wall structure of a goggle frame facing the nose for attaching the connection element and/or further comprising a second eye provided at the part of the respective side wall structure of a goggle frame opposite the part facing the nose for attaching the holding element.

13. The goggles according to claim 1, wherein the proximal end of the side wall structure, has a shape and/or size being ergonomically adapted to the shape of the patient's head in the area around the eyes.

14. The goggles according to claim 1, wherein said goggles protects the eyes of a patient from β-radiation, x-ray radiation and/or gamma radiation.

* * * * *